United States Patent [19]

Cotti

[11] 4,060,605
[45] Nov. 29, 1977

[54] WATER-SOLUBLE DERIVATIVE OF 6-DEOXY-TETRACYCLINES

[75] Inventor: Gino Cotti, Monza (Milan), Italy

[73] Assignee: Ankerfarm, S.p.A., Milan, Italy

[21] Appl. No.: 616,830

[22] Filed: Sept. 25, 1975

Related U.S. Application Data

[63] Continuation-in-part of Ser. No. 509,271, Sept. 25, 1974, abandoned.

[30] Foreign Application Priority Data

Sept. 28, 1973 Italy .................................. 29486/73

[51] Int. Cl.² ............................................. A61K 31/65
[52] U.S. Cl. .............................. 424/227; 260/559 HT; 260/351
[58] Field of Search ...................... 260/559 AT, 351; 424/227

[56] References Cited

U.S. PATENT DOCUMENTS

| | | | |
|---|---|---|---|
| 3,275,652 | 9/1966 | Martell, Jr. et al. | 424/227 |
| 3,388,161 | 6/1968 | Pavia et al. | 424/227 |
| 3,461,161 | 8/1969 | Rogalski et al. | 424/227 |
| 3,483,199 | 12/1969 | Silva | 424/227 |
| 3,637,741 | 1/1972 | Mayama et al. | 424/227 |
| 3,637,826 | 1/1972 | Intelisano | 424/227 |
| 3,835,190 | 9/1974 | Lazarera et al. | 424/227 |
| 3,847,973 | 11/1974 | Vinals et al. | 424/227 |

FOREIGN PATENT DOCUMENTS 2,246,275  9/1974  Germany .............................. 424/227

*Primary Examiner*—Delbert R. Phillips
*Attorney, Agent, or Firm*—Stevens, Davis, Miller & Mosher

[57] ABSTRACT

This invention relates to a novel water soluble derivatives of 6-deoxy-tetracyclines, particularly of doxycycline, in which a methionine group is linked to the tetracycline group through a methylene bridge, thus obtaining a derivative which is not only water soluble at neutral pH, but also endowed with outstanding properties from the point of view of the therapeutical use.

5 Claims, No Drawings

WATER-SOLUBLE DERIVATIVE OF 6-DEOXY-TETRACYCLINES

This is a continuation-in-part application of application Ser. No. 509,271 filed Sept. 25, 1974 now abandoned, entitled, A Water-Soluble Derivative of 6-Deoxy-Tetracyclines and Process For The Preparation Thereof.

The present invention has for subject matter a new antibiotic derived from the 6-deoxy-tetracyclines, which has the formula

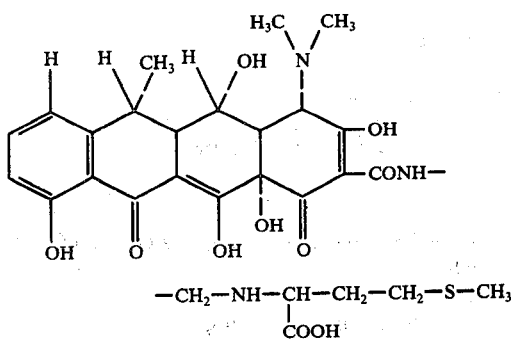

The new derivative forming subject matter of the invention is characterized by great solubility in water at neutral pH, and it can therefore be administered both per os and intramuscularly or intravenously and, in addition, preserves unaltered the antibiotic activity of deoxycycline.

The new derivative has improved patient-toleration, stability and higher blood levels as compared with both the 6-deoxy-tetracyclines and with their water soluble derivatives; furthermore, its toxicity is lower even if it maintains unaltered the antibiotic properties of the 6-deoxy-tetracyclines.

The product having the general formula I can be prepared by placing a compound of the group of the 6-deoxy-tetracyclines into contact with an equimolecular quantity of methionine, in the presence of formic aldehyde, in a polar solvent, at the temperatures and for the periods of time necessary to obtain a complete reaction.

The formaldehyde should for preference be added in the measure of one mole per mole of starting 6-deoxy-tetracycline, and can be in the form of aqueous solution, gas or even in solid form.

Suitable solvents are mono- or poly-hydroxylated alcohols containing from 1 to 4 C atoms, water, dioxane, tetrahydrofurane, methylisobutylketone, N,N' dimethylformamide.

The reaction temperatures are comprised between 10° and 80° C, but the most favourable range is 30°-40° C.

The reaction times vary from 20 minutes to 240 minutes.

The product is isolated by means of precipitation from the same solvent in which its formation takes place, or it can be precipitated with a second solvent in which it is insoluble, or it can be obtained by freeze-drying.

The product can be utilized as it is or as pharmaceutically acceptable soluble salts of mineral or organic acids, e.g. hydrochloric, hydroiodic, hydrobromic, phosphoric, metaphosphoric, nitric, sulphuric, acetic, tartaric, citric, moleic, benzoic, succinic acids, or pharmaceutically acceptable soluble mono- or poly-valent metal salts, such as alkali metal salts, e.g. sodium or potassium, or alkaline earth metal salts, e.g. calcium or magnesium, or additionally, aluminum, zinc, iron, manganese.

There is now given as Example of the preparation of the derivative of the doxycycline, but it has no limitative meaning, the process being unchanged in its essential features for the preparation of the derivative of the other 6-deoxy-tetracyclines.

EXAMPLE I

At 65° C, 4.44 g of doxycycline anhydrous base was dissolved under agitation in 140 ml of absolute ethanol.

At 35° C, addition was made of 1.5 g of methionine dissolved with 1.2 ml of 30% NaOH and 1.1 ml of 35% formic aldehyde.

The agitation was continued for 30 minutes at 35° C and for a further 30 minutes at 30° C, filtration was performed on the product obtained and washing performed with ethanol.

After vacuum drying at 40° C, there was obtained 4.85 g of product in the form of a light yellow powder, m.p.208° C. $[\alpha]_D = -55°$ (determined in solution of 1 percent 0.01 N HCl in methanol).

The pH of a 5% aqueous solution was 7.1.

The solubility of the product was more than 1 g per ml.

Composition: $C_{28}H_{35}N_3O_{10}S$ (mol. wt. 605.6).

Calculated values:

C, 55.5%; H, 5.8%; O, 26.4%; S, 5.3%; N, 7.0%.

Values found:

C, 54.6%; H, 5.9%; O, 27.1%; S, 5.4%; N, 6.5%.

There are now given the results of a few pharmacological, chemical and chemotherapeutic tests in order to illustrate the principal properties and characteristics of the product of the Example I.

A. The product is soluble in water at pH values close to neutrality; 1 g of derivative will dissolve in 0.7 ml of water.

B. The stability of the product in aqueous solution is equal or superior to that of doxycycline in analogous conditions. This is confirmed by the spectrophotometric tests.

C. The Minimal Inhibitory Concentration (MIC) of the compound of the Example I, as compared with that of doxycycline, in respect of standard bacterial strains as listed hereunder, demonstrates that, the content of doxycycline being equal, the activity of the derivative is almost identical.

|  |  | M.I.C. | |
|---|---|---|---|
|  |  | Doxycycline | Compound of Ex. I |
| S. aureus | 209P | 0.2 | 0.25 |
| S. aureus | 171G | 0.05 | 0.07 |
| S. pyrogenes | ATCC 8663 | 0.05 | 0.07 |
| S. faecalis | ATCC 8043 | 0.25 | 0.35 |
| B. arculans | ATCC 9961 | 0.05 | 0.04 |
| B. subtilis | ATCC 6633 | 0.05 | 0.04 |
| S. lutea | ATCC 10054 | 0.05 | 0.07 |
| D. pneumoniae |  | 0.01 | 0.02 |
| E. coli | 113-3 | 1.5 | 2.0 |
| E. coli | 266 | 0.75 | 1.0 |
| E. coli | ATCC 8739 | 2.0 | 2.75 |
| E. coli | ATCC 10530 | 1.25 | 1.75 |
| K. pneumoniae | 132 | 1.5 | 2.25 |
| P. vulgaris | ATCC 9920 | >50 | 50 |
| P. rettgerii | ATCC 9250 | 1.75 | 2.5 |
| P. mirabilis | ATCC 9921 | >100 | 100 |

D. Chemotherapeutic activity of the compound of the Example I expressed as $PD_{50}$ in mice infected with various bacterial strains.

| Infection | Route (a) | Dose (b) | Compound of Ex. I $PD_{50}$ mg/kg | Δ%(c) | Doxycycline $PD_{50}$ mg/kg |
|---|---|---|---|---|---|
| S. aureus (d) | oral | S. | 9.04 | — | 7.48 |
| | intravenous | S. | 7.11 | 78.6 | — |
| | subcutaneous | M. | 1.67 | 16.2 | 2.21 |
| S. pyrogenes 8668 | oral | S. | 7.55 | — | 5.74 |
| S. Pyrogenes 8668 | intravenous | S. | 5.41 | 71.6 | — |
| S. pyrogenes (d) | oral | S. | 0.64 | — | 0.51 |
| | intravenous | S. | 0.47 | 73.3 | — |
| Infection | Route (a) | Dose (b) | $PD_{50}$ mg/kg | %(c) | Doxycycline |
| E. coli 266 | oral | S. | 52.1 | — | 38.0 |
| | intravenous | S. | 36.7 | 70.4 | — |
| E. coli (d) | oral | S. | 20.4 | — | 16.2 |
| | intravenous | S. | 14.6 | 71.5 | — |
| K. pneumoniae | subcutaneous | S. | 1.32 | — | — |
| | intravenous | S. | 1.03 | 78.0 | — |

(a) = Route of administration: oral, intravenous, subcutaneous
(b) = Doses: single (S) or multiple (M)
(c) = decrease in percentage of oral $PD_{50}$
(d) = Strains of clinical origin
(e) = Decrease in percentage of subcutaneous $PD_{50}$ E. The blood level of the product of the Example I in mice, rats and rabbits after a single oral dose of 12.5 mg/kg is equal or superior, in the various time intervals, to the blood level of doxycycline in the same conditions.

F. Acute toxicity ($LD_{50}$) of the compound of the Example I in mice and rats.

Data compared with data for Doxycycline (in brackets).

| Animal species | Route | $LD_{50}$ mg/kg | |
|---|---|---|---|
| Mouse | oral | >2000* | (>2000)* |
| | intravenous | 394 | (257) |
| | | 670 | (425) |
| Rat | oral | >3000* | (>3000)* |
| | | 582 | (370) |

*Tests limited to a maximum dose of 2.0 g/kg or 3.0 g/kg, thereafter suspended inasmuch as not of great significance.

The following are some specific Examples of the preparation of formulations suitable for pharmaceutical use.

EXAMPLE II

Injectable Preparation 150 mg, of the compound prepared in the Example I, equivalent to 100 mg of doxycycline base, are admixed with 20 mg of solid NaCl. From this mixture a 5% dextrose solution for slow intravenous perfusion is prepared.

EXAMPLE III

Capsules for Oral Administration

Compound of Example I: 150 mg
Mg stearate: 3 mg
Lactose: 50 mg
Talc: 5 mg
Corn starch, q.s. to 300 mg.

EXAMPLE IV

Powder for Extemporaneous Solution for Oral Administration.

Compound of Example I: 1.5 g (equivalent to 1.0 g of doxycycline base)
Na benzoate: 0.06 g
Na carboxymethyl cellulose: 0.16 g
Sugar: 35 g
Strawberry spirit: 0.05 g
Colorant E 127: 0.065 g.

I claim:

1. A compound with the formula:

(I)

[chemical structure of tetracycline derivative with substituent $-CH_2-NH-CH-CH_2-CH_2-S-CH_3$ with $COOH$ branch]

2. The compound of claim 1 in the form of a pharmaceutically acceptable soluble salt of an organic or inorganic acid, or a pharmaceutically acceptable soluble mono- or poly-valent metal salt.

3. The compound of claim 2 wherein the metal of the metal salt is selected from the group consisting of sodium, potassium, calcium, magnesium, aluminium, zinc, iron and manganese.

4. An antibacterial composition comprising an antibacterial amount of compound of claim 1 and a pharmaceutical acceptable vehicle.

5. The composition of claim 4 wherein the vehicle is water.

* * * * *